United States Patent
Tu et al.

(10) Patent No.: US 11,049,246 B2
(45) Date of Patent: Jun. 29, 2021

(54) RAPID CALCULATION METHOD AND SYSTEM FOR PLAQUE STABILITY INDEX BASED ON MEDICAL IMAGE SEQUENCE

(71) Applicant: SHAGHAI JIAO TONG UNIVERSITY, Shanghai (CN)

(72) Inventors: Shengxian Tu, Shanghai (CN); Xinlei Wu, Shanghai (CN); Su Zhang, Shanghai (CN); Jiayue Huang, Shanghai (CN)

(73) Assignee: SHAGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 16/768,545

(22) PCT Filed: May 29, 2018

(86) PCT No.: PCT/CN2018/088861
§ 371 (c)(1),
(2) Date: May 29, 2020

(87) PCT Pub. No.: WO2019/109607
PCT Pub. Date: Jun. 13, 2019

(65) Prior Publication Data
US 2020/0320688 A1    Oct. 8, 2020

(30) Foreign Application Priority Data
Dec. 7, 2017    (CN) .......................... 201711282886.3

(51) Int. Cl.
*G06T 7/00*    (2017.01)
*G06T 7/149*   (2017.01)
(Continued)

(52) U.S. Cl.
CPC ............ *G06T 7/0012* (2013.01); *G06T 7/149* (2017.01); *G06T 7/33* (2017.01); *G06T 11/003* (2013.01); *G06T 2207/30101* (2013.01)

(58) Field of Classification Search
None
See application file for complete search history.

(56) References Cited

U.S. PATENT DOCUMENTS 10,631,718 B2 * 4/2020 Petroff ................. A61B 5/0084
10,748,289 B2 * 8/2020 Tolkowsky ............ A61B 6/504
(Continued)

FOREIGN PATENT DOCUMENTS

CN    106570313 B    3/2019

OTHER PUBLICATIONS

CN106570313B Method and system for obtaining four-dimensional blood vessel deformation behavior and in-vivo stress of blood vessel wall ; Applicants Shanghai Jiaotong University; Fuwai Hospital, Chinese Academy of Medical Sciences Inventors Oct. 18, 2016 (Year: 2016).*

*Primary Examiner* — Nancy Bitar
(74) *Attorney, Agent, or Firm* — Gearhart Law LLC; David Postolski, Esq.

(57) ABSTRACT

The present invention provides a rapid calculation method and system for a plaque stability index based on a medical image sequence. The system includes an image acquisition module, an image receiving module, an image processing module, a finite element calculation module and a result visualization module. The image acquisition module and the image receiving module are configured to acquire, receive and transmit a dynamic two-dimensional vascular image sequence; the image processing module is configured to acquire a space-transformational displacement field function by taking a local feature or a global image as a registration based on dynamic information of real-time deformation of (Continued)

an artery under a two-dimensional image; and the finite element calculation module is configured to acquire a time-dependent vascular lumen diameter sequence and a contour deformation parameter as well as a mechanical index by calculation performed by virtue of the above-mentioned displacement field function.

9 Claims, 2 Drawing Sheets

(51) Int. Cl.
  *G06T 7/33* (2017.01)
  *G06T 11/00* (2006.01)

(56) References Cited

U.S. PATENT DOCUMENTS

| | | | |
|---|---|---|---|
| 2006/0100502 A1* | 5/2006 | Chen | A61B 6/504 600/419 |
| 2007/0165916 A1* | 7/2007 | Cloutier | G06K 9/6278 382/128 |
| 2014/0100451 A1* | 4/2014 | Tolkowsky | G06T 5/50 600/424 |
| 2014/0121513 A1* | 5/2014 | Tolkowsky | A61B 6/481 600/431 |

* cited by examiner

RAPID CALCULATION METHOD AND SYSTEM FOR PLAQUE STABILITY INDEX BASED ON MEDICAL IMAGE SEQUENCE

CROSS REFERENCE TO RELATED APPLICATION

The present application is a U.S. national phase application of a PCT Application No. PCT/CN2018/088861 filed on May 29, 2018 which claims priority to the Chinese patent application No. 201711282886.3 filed with SIPO on Dec. 7, 2017 and entitled "Rapid Calculation Method and System for Plaque Stability Index Based on Medical Image Sequence", the disclosures of which are incorporated herein by reference in their entirety.

TECHNICAL FIELD

The present invention is applied to the field of medical instruments and in particular relates to an accurate, rapid and noninvasive calculation method and system for a two-dimensional vascular lumen deformation behavior, namely a time-dependent lumen geometry and boundary contour strain parameter, based on a medical image sequence.

BACKGROUND

For vascular plaque evaluation commonly used in clinic at present, information such as the stenosis degree of a two-dimensional lumen as well as the size and position of a plaque is determined in an imaging way such as intravascular ultrasound, optical coherence tomography, X-ray angiography and CT angiography. However, various researches show that there is no direct relationship between a morphological index of the plaque and the high risk of the plaque rupture, for example, a higher diameter stenosis of a coronary artery diameter does not indicate a higher occurrence rate of plaque rupture. An arterial wall cyclically deforms under the actions of factors such as pulse blood pressure, peripheral soft tissue constraints and (or) cyclic myocardial diastole and systole. In this way, a morphological index of an artery may have a certain variability and cyclicity at a certain moment.

Although the deformation performance of a vascular wall is evaluated from the aspects such as different medical image sources, different spatial dimensions and different calculation methods by using a technical method based on a medical image sequence with vascular wall deformation and the invention patent, the technical method and the invention patent still have various limitations or defects and even cannot be better applied to clinical practice due to poor operability.

A patent document CN101474082B discloses an elastic analysis method for a vascular wall based on the finite deformation theory, which is used for analyzing elastic properties of the vascular wall by calculating a strain feature value of the vascular wall under a certain pressure in an intravascular ultrasound (IVUS) image. An ultrasonic probe is mainly adopted to suspend on a specific position in a vascular lumen to acquire images of a plurality of cardiac cycles, a corresponding point matched with a marking point in an original image is researched by utilizing a template matching method, and then, the elasticity of the vascular wall is calculated by segmentation based on a finite element method. However, the image acquisition of a time-dependent vessel at relatively high frequency cannot be implemented in a relatively short cardiac cycle due to overlong ultrasound acquisition time, and therefore, such an ultrasound-based Doppler principle and living tissue combined elastic imaging method is not suitable for application within a coronary heart disease.

A patent document CN106974622A discloses a method and system of measuring plaque stability measuring method and system based on an optical coherence tomography (OCT), which are used for processing and analyzing a coronary artery image including fibrous cap, macrophage, lipid and the like. A probe is mainly adopted to suspend on a certain position in a vascular lumen to acquire image results of a plurality of cardiac cycles so as to acquire information about a size of a lipid nucleus and a strain of a plaque, and then, the plaque stability is comprehensively analyzed in combination with pathological indexes of the plaque. However, even if multiple frames of images are acquired by controlling the suspending position of the probe, images of front and rear frames may generate longitudinal variation due to greater longitudinal stretch of a vessel in the cardiac cycles. In addition, similar to an image, adopting an image of a cross section of a vessel on a specific position, in the vascular lumen, for various stenosis lesions (such as a diffuse lesion as well as a stenosis lesion) in a longitudinal direction of the vessel, images on different positions are required to be acquired and evaluated for many times to result in operation complexity.

A patent document CN106570313A discloses a method and system for acquiring a four-dimensional vascular deformation behavior and an in-vivo stress of a vascular wall. Due to the combination of a three-dimensional reconstruction technology for a coronary angiography image and a discrete approximation theory in the method, simulating calculation for a large deformation behavior of the vascular wall in a cardiac cycle is implemented, the in-vivo stress of the vascular wall is acquired, and kinematic features of the vascular wall are quantitatively described, so that the stability of a three-dimensional plaque may be evaluated. However, high manual acting and implementation complexity exist due to an in-vivo four-dimensional vessel deformation behavior implemented after three-dimensional reconstruction at multiple moments, and defects such as a certain error or multiple error accumulations exist due to space conversion caused by multiple three-dimensional reconstructions at different moments.

In addition, a rapid calculation method and system for acquiring a two-dimensional lumen deformation parameter based on a medical image sequence and evaluating plaque stability has not been provided at present.

SUMMARY

In view of this, the present invention provides a rapid calculation method and system for an arterial plaque stability index based on the medical image sequence. A real-time dynamic deformation performance parameters of a two-dimensional pathological lumen (or a superficial wall of lesion) is acquired by utilizing time-dependent information of an arterial lumen contour in a two-dimensional plane in combination with medical image processing technology and the finite element method on the basis of dynamic medical image sequence with cyclic vessel deformation, and furthermore, an index for representing the plaque stability is determined. In a word, the rapid calculation method and system, which are high in efficiency and strong in operability, for plaque stability evaluation may be implemented based on the above information.

Specifically, the present invention provides the following technical solutions:

On the one hand, the present invention provides a rapid calculation system for a plaque stability index based on a medical image sequence, and the system includes:

an image acquisition module, mainly configured to acquire an image and generate a dynamic image sequence;

an image receiving module, configured to receive the image sequence generated by the image acquisition module and transmit the image sequence to an image processing module;

the image processing module, configured to process the received image sequence, wherein the processing includes segmentation and registration of a lumen contour; the segmentation of the lumen contour includes rapid segmentation of a normal lumen and a stenotic lumen, and the registration of a lumen specifically refers to performing registration according to a feature space of the same vascular segment at different moments to generate a displacement field function; and a finite element calculation module, configured to perform finite element calculation on a two-dimensional vascular lumen by utilizing the above-mentioned displacement field function and perform calculation by selecting a vascular lumen at a certain moment as an initial state to obtain a time-dependent parameter and cloud picture including a function that a lumen diameter sequence or area is changed with time, and a linear strain of the lumen contour.

Preferably, the system further includes a result visualization module, configured to display corresponding analysis results of the image processing module and the finite element calculation module as well as an evaluation index for the plaque stability.

Preferably, the image processing module further includes the following sub-modules:

an image segmentation module, configured to rapidly segment the lumen contour and grade a contour of a region where a normal lumen segment and a stenotic lumen segment are located to implement graded modeling and acquire a graded vascular segmentation model; and an image registration module, configured to register a vascular contour at multiple moments and perform contour feature or full image registration on the graded vascular segmentation model at the multiple moments to acquire a displacement field function generated in a registration process.

Preferably, the correlation of the plaque stability is evaluated by a morphological index of a plaque on the basis of a finite element calculation result of large sample data in combination with an intravascular image, a range of a finite element result parameter corresponding to a stability degree of the plaque is established, and finally, stability information of a vascular stenotic segment may be directly prompted by the result visualization module.

Preferably, the image receiving module, the image processing module, the finite element calculation module, and the result visualization module in the system are integrated together to implement functions such as automatic processing of an image sequence, a semi-automatic division of a region of interest, and result display.

Preferably, the system adopts real-time data transmission, a rapid image processing technology and a simplified finite element calculation method during in-vivo image processing, so that plaque stability evaluation with high efficiency and strong operability is implemented.

In addition, on the other hand, the present invention further provides a rapid calculation method for a plaque stability index based on a medical image sequence, and the method includes:

step 1, determining starting and ending positions of a vessel of interest, and defining a vessel between the starting and ending positions as a first-level segment, wherein preferably, anatomical mark points (bifurcations) are used as the starting and ending positions of the vessel of interest, a coronary artery is taken as an example of a vessel herein, but the vessel is not limited to the coronary artery, and all vessels with dynamic cyclic deformation are applicable herein;

step 2, acquiring a medical image sequence, and determining a plurality of feature moments of the vessel of interest in a deformation cycle, wherein the medical image sequence includes complete images of a plurality of cycles of vessels; and preferably, several of the feature moments in the deformation cycle may be determined at the above-mentioned feature moments in combination with a deformation rule of the vessels or by virtue of additional data information such as an electrocardiogram;

step 3, performing lumen contour segmentation on the same vessel with different morphologies in frame images corresponding to different feature moments in step 2, determining starting and ending positions of a stenotic segment in the vessel of interest, and defining the stenotic segment as a second-level segment, wherein a coronary artery arteriography image which has the medical image sequence is taken as an example herein, but the coronary artery arteriography image is not limited to have the medical image sequence, and all medical image sequences with dynamic cyclic deformation of the vessels are applicable herein;

step 4, respectively establishing geometric models of a closed two-dimensional vascular lumen by using the first-level segment and the second-level segment in combination with a boundary contour line, and determining two regions of interest of the first-level segment and the second-level segment;

step 5, normalizing vessels with different lengths in different frame images by taking the length of a center line as a standard; and performing grid isomorphic discretization based on the normalized vessel length to establish a finite element model of a two-dimensional vascular lumen, firstly, performing coarse registration on the first-level segment, further performing fine registration on the second-level segment, and then, acquiring a displacement field function generated by a registration result;

step 6, applying the displacement field function to the finite element model of the two-dimensional vascular lumen acquired in step 5 and solving the displacement field function so as to acquire a cyclic time-dependent geometric deformation parameter of the lumen, a strain parameter of a lumen contour, and a cloud picture; and step 7, performing correlation analysis based on the cyclic time-dependent geometric deformation parameter of the lumen and the strain parameter of the lumen contour in step 6 in combination with plaque stability sample data, and performing calculation to obtain a plaque stability result.

Preferably, the feature moments in step 2 are determined according to demarcation points of various wavebands of an electrocardiogram; or for other cyclic deformation arteries, such as a renal artery, of which key time points cannot be detected with the assistance of the electrocardiogram, a plurality of key time points are selected according to deformation features in the image sequence, and a cycle length and a time interval between every two adjacent time points are acquired, so that the feature moments are determined.

Preferably, step 3 further includes:

step 301, generating a center line of a vessel and a reference lumen as well as a series of diameter sequences in a longitudinal direction of the vessel and vertical to the center line while performing lumen contour segmentation on the vessel; and step 302, setting a diameter stenosis percentage threshold, calculating a diameter stenosis percentage DS % (x) of the vessel of interest along a current position of the center line of the vessel, and taking starting and ending positions of a vascular segment meeting a requirement for the diameter stenosis percentage threshold as starting and ending positions of the second-level segment.

A calculation formula of DS % (x) is as follows:

$$DS\ \%(x) = \left(1 - \frac{D_{act}(x)}{D_{ref}(x)}\right) \times 100 = \left(1 - \frac{D_{act}(x)}{(D_{pro} - D_{dis})x/L_{cen}}\right) \times 100;$$

In the formula, $D_{act}$ is an actual lumen diameter, $D_{ref}$ is a reference lumen diameter, $D_{pro}$ and $D_{dis}$ are respectively a near-end lumen diameter and a far-end lumen diameter, $L_{cen}$ is a total length of a center line, and x is a length of a center line from a current section position to a near end section.

Preferably, step 4 further includes:

establishing a feature space for image registration, wherein features included by the feature space includes a lumen contour, a center line of a lumen and a diameter sequence; and generating an equivalent diameter sequence after normalization.

Further preferably, the normalization may adopt a method such as a bilinear interpolation method and a cubic convolution interpolation method.

Preferably, step 5 further includes:

performing feature search in the above-mentioned feature space according to a preset search strategy; and setting a similarity threshold of the first-level segment and the second-level segment of the vessel as a quantization standard in a registration process according to a preset similarity measurement criterion.

Further preferably, the search strategy may be a search algorithm such as a golden section method and a gradient descent method.

Further preferably, the similarity measurement criterion may be calculated by adopting a method such as a gray difference square sum, a maximal information coefficient and a Euclidean distance among feature points.

Preferably, step 6 further includes:

step 601, taking a geometric model of a two-dimensional lumen at a certain time point as an initial configuration, and performing structured grid discretization on the geometric model of the two-dimensional lumen at the certain time point, wherein further preferably, the initial configuration may be an initial configuration at the moment when the vessel is shortest; and after grid discretization, a grid may be subjected to smoothing preprocessing by adopting a Laplacian algorithm, for example; and step 602, taking a finite element method as an image registration method, and when a similarity threshold of a stenotic segment and/or a normal segment is met, acquiring the displacement field function between adjacent moments until traversing a complete vascular deformation cycle so as to form a displacement path of a point cloud in a vascular deformation cycle.

Preferably, in step 7, the strain parameter of the lumen contour includes a maximum principal strain, a minimum principal strain, an out-of-plane strain and the like. Further preferably, parameters, such as an extreme value, a mean value and an amplitude, reflecting dynamic cyclic features are used as secondary result parameters.

Preferably, in step 7, the plaque stability is calculated by adopting the following formula:

$$S = \ln\left(c_1 * \frac{A}{A_0}\right) + \ln(c_2 * \overline{D_\varepsilon}) + \ln\left(c_3 * \frac{\overline{\varepsilon}}{\varepsilon_{max}}\right)$$

In the formula, A is a minimum stenosis area, $\overline{D_\varepsilon}$ is a mean value of a diameter strain on a minimum stenosis position, $\varepsilon_{max}$ and $\overline{\varepsilon}$ are respectively a maximum value and a mean value of a lumen contour strain, $C_i$, i=1, 2 and 3 are fitting parameters, and $A_0$ is the area of the reference lumen on the minimum stenosis position.

Compared with the prior arts of two inventions CN101474082B and CN106974622A, the beneficial effects of the technical solution of the present invention are as follows: The global deformation of the vessel is observed in real time by virtue of extravascular imaging instead of the deformation of a certain position in the vascular lumen, so that the vascular deformation is observed more comprehensively and completely. Compared with an invention patent CN106570313A, the beneficial effects of the technical solution of the present invention are as follows: The spatial dimension of the calculated vessel is reduced, and only a vascular deformation condition in a two-dimensional imaging plane is taken into account, so that defects such as high workload, low efficiency, space conversion error accumulation and poor application operability caused by three-dimensional reconstruction of the vessel at multiple moments are avoided, and the calculation efficiency in unique consideration of the two-dimensional vascular lumen deformation in a plane is higher and more accurate. In addition, on the one hand, rapid image segmentation, registration and calculation are directly performed on a two-dimensional image by utilizing deformation information of a vascular lumen in a traditional medical image sequence, and the dynamic change and contour deformation performance of a lumen diameter sequence are calculated by using the image processing technology and the finite element method, so that a deformation behavior of the two-dimensional vascular lumen in the plane may be acquired rapidly, accurately and effectively. On the other hand, the novel method and system for directly reflecting the plaque stability evaluation of a global vessel by dynamic parameters of vascular deformation are established in combination with plaque stability image features. Therefore, the original medical image function is implemented, meanwhile, a function of more directly and efficiently performing quantitative evaluation on the plaque stability is added, in addition, the cost is reduced, the time is saved, and a brand new, efficient and feasible method is provided for measuring the plaque stability.

BRIEF DESCRIPTION OF THE DRAWINGS

To describe the technical solutions of the embodiments of the present invention or the prior art more clearly, the accompanying drawings required for describing the embodiments or the prior art will be simply introduced below. Apparently, the accompanying drawings in the following description show only some embodiments of the present invention, and a person of ordinary skill in the art may still acquire other accompanying drawings from these accompanying drawings without creative efforts.

DETAILED DESCRIPTION

The technical solutions in the embodiments of the present invention are described in detail below in combination with the accompanying drawings. It should be known by a person skilled in the art that the following specific embodiments or specific implementations are a series of optimized setting ways listed for further explaining the specific content of the invention, while these setting ways may be combined or associated with each other unless the present invention clearly proposes that some specific embodiments or implementations or a certain specific embodiment or implementation cannot be associated or used together with other embodiments or implementations. Meanwhile, the undermentioned specific embodiments or implementations are only used as the optimized setting ways, but are not regarded as limitations to the scope of protection of the present invention.

Embodiment 1

The present invention provides a rapid calculation method for a plaque stability index based on a medical image sequence, and the rapid calculation method for the plaque stability index when a coronary artery arteriography image sequence is adopted as a medical image source is described below in a specific embodiment. In this embodiment, an acquired sequence image of an anterior descending branch of a coronary artery is taken as an example, the person skilled in the art should be understood that vascular image data of a specific part is used as an example herein, but the specific part or vessel should not be regarded as a limitation to the scope of protection of the present invention.

In a specific embodiment, the method includes the following steps: An image receiving module reads a two-dimensional arteriography image sequence with a complete cardiac cycle of an anterior descending branch of a coronary artery; starting and ending positions of a vessel are determined, and a vessel between the starting and ending positions is defined as a first-level segment. Preferably, the above-mentioned starting and ending positions may be selected as anatomic mark points of bifurcations of a near end and a far end in the anterior descending branch.

Figure 1:
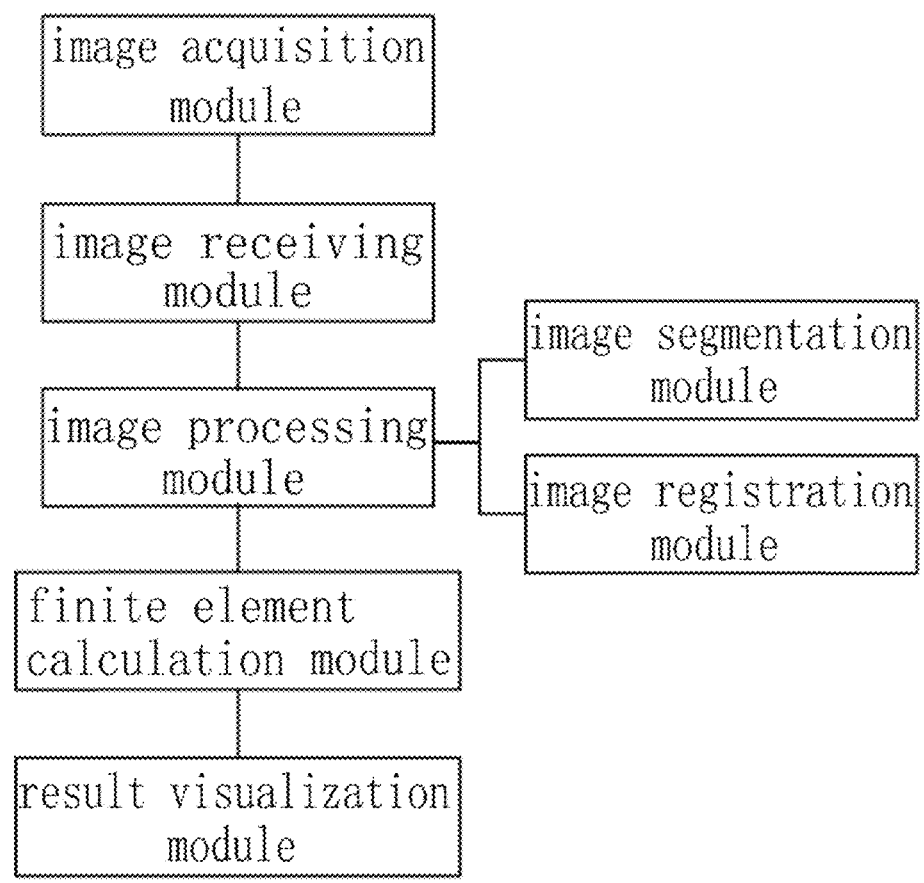
FIG. 1 is a frame diagram of a rapid analysis system for an arterial plaque stability index based on a medical image sequence in the present invention.

In a specific embodiment, at least one feature moment in a complete cycle is selected, for example, in the embodiment, the method further includes the following steps: The following three feature moments including a diastole end, a systole end and a resting end are determined to be selected in a deformation cycle in combination with a deformation rule of the vessel, as shown in FIG. 1; and rapid lumen contour segmentation is performed on vessels with different morphologies in frames of images corresponding to the plurality of above-mentioned different feature moments to extract a plurality of groups of corresponding contours as well as a center line of a lumen and longitudinal diameter sequences of the vessels, so that starting and ending positions of a stenotic segment in each vessel in a vessel of interest are determined, and a vessel between the starting and ending positions of the segment is defined as a second-level segment.

In a specific embodiment, the method includes the following step: The vessels with different lengths under different frames are normalized by taking the length of a center line as a standard, selecting a vessel with the shortest center line as a reference and controlling the sum of key points fixed under each frame by utilizing a re-sampling algorithm with regard to point sets on vascular contours under different frames.

In a specific embodiment, the method further includes the following step: Grid isomorphic discretization is performed based on the normalized vessel length to establish a finite element model of a two-dimensional vascular lumen; and registration implemented by taking important information (partial detail information) such as a contour of a stenotic segment and a diameter sequence as well as a contour of the two-dimensional vascular lumen (full information) as feature spaces is performed by using a finite element method. In the above-mentioned registration calculation, firstly, coarse registration on the first-level segment is performed, and then, fine registration on the second-level segment is further performed. In the coarse registration on the first-level segment, an image gray difference square sum function is used as a similarity measurement function:

$$E = \frac{1}{|\Omega|} \sum_{x \in \Omega} (I_f(T(x)) - I_m(x))^2;$$

$\Omega$ is a region of interest of the first-level segment of a vessel, $|\Omega|$ is a total pixel in the region, $T(x)$ is a displacement field function (space conversion function), $I_f$ is a previous-frame reference image, and $I_m$ is a next-frame floating image.

In the fine registration on the second-level segment, a registration transform function is optimized on the above-mentioned basis in combination with the control on feature points and the diameter sequence, and a distance among the feature points is used as a similarity measurement function:

$$L(T(x)) = \sum_{i=1}^{n} \left( p_{I_f^i} - T(p_{I_m^i}) \right)^2;$$

$P_{I_f^i}$ and $P_{I_m^i}$ are respectively key point sets in the reference image and the floating image, and the displacement field function T is:

$$T(x) = \begin{cases} x + \sum_{i=1}^{n} (x - p_{I_m^i}), & x \text{ is on the counter} \\ x + \sum_{j=1}^{k-1} \frac{j}{k} a_j, & x \text{ is in the lumen} \end{cases}$$

Herein, $a_j$ is an interactivity diameter sequence vector, and k is a total score in a diameter direction.

Figure 2:
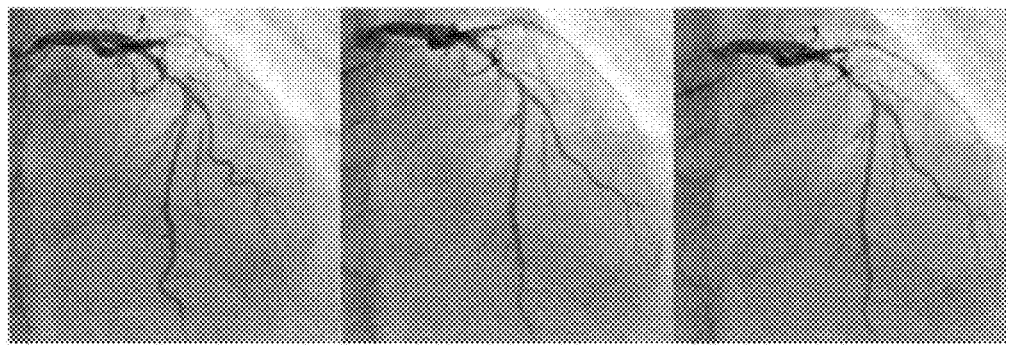
FIG. 2 is an original two-dimensional arteriography image sequence in Embodiment 1 of the present invention.

In a specific embodiment, the method further includes the following steps: The displacement field function is applied to the above-mentioned acquired finite element model of the two-dimensional vascular lumen and is solved by selecting an explicit solution method based on time marching so as to acquire a cyclic time-dependent geometric deformation parameter of the lumen, a strain parameter of a lumen contour (pathological superficial wall) and a cloud picture, as shown in FIG. 2.

In a specific embodiment, the method further includes the following step: A center line of a pathological vessel and a reference lumen as well as a series of diameter sequences in a longitudinal direction of the vessel and vertical to the center line are generated while rapid lumen contour segmentation on the vessel is performed.

In a specific embodiment, the method further includes the following step: For starting and ending positions of the two-level segment and the stenotic segment in the vessel of interest, a diameter stenosis percentage DS % (x) along a current position of the center line of the vessel is introduced, and a calculation formula thereof is as follows:

$$DS\ \%(x) = \left(1 - \frac{D_{act}(x)}{D_{ref}(x)}\right) \times 100 = \left(1 - \frac{D_{act}(x)}{(D_{pro} - D_{dis})x/L_{cen}}\right) \times 100$$

In the formula, $D_{act}$ is an actual lumen diameter, $D_{ref}$ is a reference lumen diameter, $D_{pro}$ and $D_{dis}$ are respectively a near-end lumen diameter and a far-end lumen diameter, $L_{cen}$ is a total length of the center line, and x is a length of a center line from a current section position to a near end section.

Herein, DS % (x) serving as a threshold for judgment may select 50%. Certainly, the threshold for judgment may also be regulated to other values according to a judgment criterion basis or vascular features in different regions.

In a specific embodiment, the method further includes the following steps: The two-dimensional lumen contour is used as a feature space for registration of a subsequent image, and the vessels with the different lengths are normalized by utilizing an optimized re-sampling algorithm.

In a specific embodiment, the method further includes the following steps: Rapid and effective feature search is performed in the above-mentioned feature spaces by adopting a golden section search algorithm as a search strategy; and a gray difference square sum function and a Euclidean distance may be adopted as similarity measurement criterions, and when a manner of the Euclidean distance is adopted, the sum of the Euclidean distances of feature points of the stenotic segment may be set as an index in a registration process, for example, a Euclidean distance is set as a similarity measurement threshold which is used as a judgment standard.

In a specific embodiment, the method further includes the following step: A geometric model of a two-dimensional lumen at a systole end is used as an initial configuration, preferably, structured grid discretization is performed on the geometric model of the two-dimensional lumen at the systole end, smoothing preprocessing may be performed on a grid by adopting a Laplacian algorithm, and preferably, three iterations are selected.

In a specific embodiment, the method further includes the following step: A two-dimensional image registration method may adopt a finite element method, and when a similarity measurement threshold of the Euclidean distance of the stenotic segment is met, the displacement field function between adjacent moments is acquired until a cycle is traversed so as to form a displacement path of a point cloud in a two-dimensional model in a vascular deformation cycle.

Figure 3:
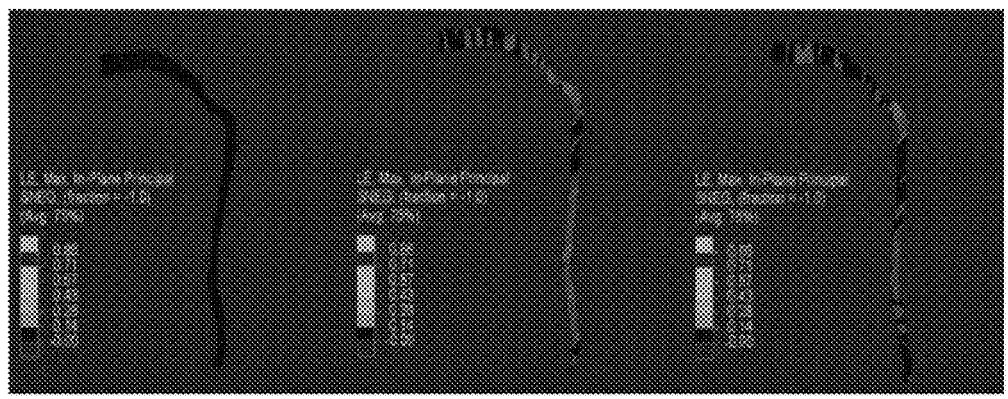
FIG. 3 is a strain parameter result of a real lumen in Embodiment 1 of the present invention.
Figure 4:
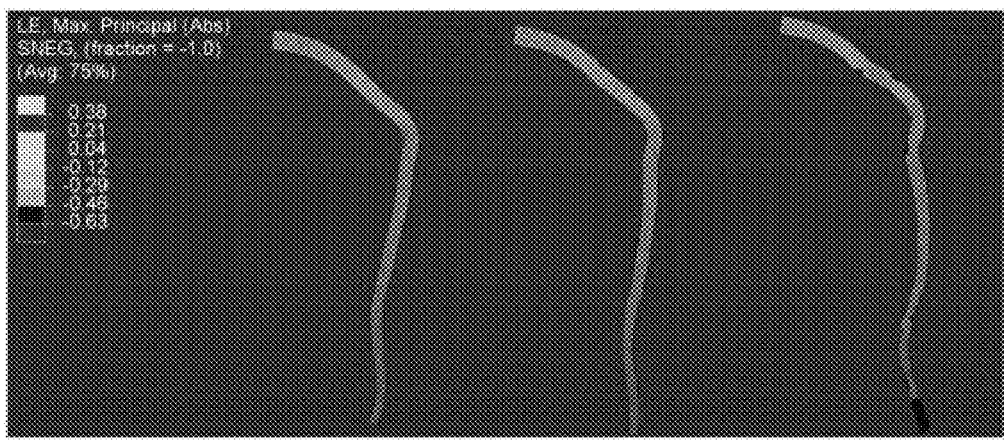
FIG. 4 is a strain parameter result of a reference lumen in Embodiment 1 of the present invention.

In a specific embodiment, the method further includes the following steps: An index such as an out-of-plane strain in the strain parameter of a pathological lumen contour (superficial wall) is adopted as an example result, as shown in FIG. 3; and an out-of-plane strain index of the reference lumen is adopted as the other example result, as shown in FIG. 4.

Embodiment 2

In another specific embodiment, an algorithm for judging and evaluating plaque stability in the present invention is described with a specific application scene.

A plaque stability index is obtained by cyclic deformation analysis for a two-dimensional vessel by using the method provided by the present invention, namely data for judging the plaque stability is calculated. Specifically, the method may also be implemented by the following steps:

In a specific implementation, a maximum principal strain in a strain parameter of a diameter of a smallest stenosis position of a pathological lumen is used as a specific index. Preferably, a mean value for reflecting a dynamic cyclic feature is selected as a secondary result parameter. Certainly, the specific index and the secondary result parameter herein may be adjustably selected. For example, the maximum principal strain in the strain parameter may be changed into a parameter such as a minimum principal strain and an out-of-plane strain.

In a specific implementation, a maximum principal strain in a strain parameter of a superficial wall of a pathological lumen contour is used as the specific index. Preferably, a maximum value, a mean value, an amplitude and the like are selected as secondary result parameters, and the selection of the secondary result parameters may be adjusted as required.

In a specific implementation, after large sample and large database analysis, a multi-factor correlation expression established by taking plaque stability S as a function value as well as the minimum stenosis area A of a lesion, a mean value $\overline{D_\varepsilon}$ of a diameter strain at a minimum stenosis position, a maximum lumen contour strain $\varepsilon_{max}$ and a mean value $\overline{\varepsilon}$ as variables is fitted as:

$$S = \ln\left(c_1 * \frac{A}{A_0}\right) + \ln(c_2 * \overline{D_\varepsilon}) + \ln\left(c_3 * \frac{\overline{\varepsilon}}{\varepsilon_{max}}\right)$$

Herein, $C_i$, i=1, 2 and 3 are fitting parameters, and $A_0$ is the area of the reference lumen on the minimum stenosis position.

In a specific implementation, new results of the above-mentioned variables are introduced to a plaque stability index function expression to obtain a plaque stability index. The value of S ranges from 0 to 1, and the smaller the value of S is, the more instable a plaque is.

Embodiment 3

In a further specific embodiment, the present invention further provides a rapid calculation system for a plaque stability index based on a medical image sequence, and the system includes:

an image acquisition module, mainly configured to acquire an image and generate a dynamic image sequence;

an image receiving module, configured to receive the image sequence generated by the image acquiring module and transmit the image sequence to an image processing module;

the image processing module, configured to process the received image sequence, wherein the processing includes segmentation and registration of a lumen contour; the segmentation of the lumen contour includes rapid segmentation of a normal lumen and a stenotic lumen, and the registration of a lumen specifically refers to performing registration according to a feature space on the same vascular segment at different moments to generate a displacement field function;

a finite element calculation module, configured to perform finite element calculation on a two-dimensional vascular lumen by utilizing the above-mentioned displacement field function, and perform calculation by selecting a vascular lumen at a certain moment as an initial state to obtain a time-dependent parameter and cloud picture including a function that a lumen diameter sequence or area is changed with time and a linear strain of the lumen contour; and a result visualization module, configured to display corresponding analysis results of the image processing module and the finite element calculation module as well as an evaluation index for the plaque stability.

Preferably, the image processing module further includes the following sub-modules:

an image segmentation module, configured to rapidly segment the lumen contour and grade a contour of a region where a normal lumen segment and a stenotic lumen segment are located to implement graded modeling and acquire a graded vascular segmentation model; and an image registration module, configured to register a vascular contour at multiple moments and perform contour feature or global image registration on the graded vascular segmentation model at the multiple moments to acquire a displacement field function generated in a registration process.

Preferably, the correlation of the plaque stability is evaluated by a morphological index of the plaque on the basis of a finite element calculation result of large sample data in combination with an intravascular image, a range of a finite element result parameter corresponding to a stability degree of the plaque is established, and finally, stability information of a vascular stenotic segment may be directly prompted on the result visualization module.

Preferably, the image receiving module, the image processing module, the finite element calculation module and the result visualization module in the system are integrated together to implement functions such as automatic processing of an image sequence, a semi-automatic division of a region of interest and result display.

Preferably, the system adopts real-time data transmission, a rapid image processing technology and a simplified finite element calculation method during in-vivo image processing, so that plaque stability evaluation with high efficiency and strong operability is implemented.

Preferably, the finite element calculation module performs finite element calculation by utilizing the above-mentioned displacement field function. A vascular lumen at an initial moment is selected, time-dependent parameters including a function that a lumen diameter sequence or area is changed with time and a linear strain (including various calculation strain indexes such as a maximum principal strain, a minimum principal strain and an out-of-plane strain) of a superficial wall as well as distribution are acquired through the module.

Compared with the prior art, the beneficial effects of the technical solution of the present invention are as follows: The dynamic change of a lumen morphology and the strain performance of the contour are implemented by virtue of deformation information of a vascular lumen in a traditional medical image sequence and utilizing the medical image processing technology and the finite element method, so that the novel method and system for measuring plaque stability are established. According to the present invention, image segmentation and registration are directly performed on an original two-dimensional image, so that not only may a deformation behavior of the two-dimensional vascular lumen in the plane be acquired rapidly, accurately and effectively, but also defects such as low efficiency, space conversion error accumulation and poor application operability caused by three-dimensional reconstruction of a vessel are avoided. The original medical image function is implemented, meanwhile, the function of more directly and efficiently performing quantitative evaluation on the plaque stability is added. In addition, the cost is reduced, the time is saved, and the brand new, efficient and feasible method is provided for evaluating the plaque stability.

The person of ordinary skill in the art can understand that all or parts of processes in the methods in the above-mentioned embodiments can be completed by relevant hardware instructed by computer programs, all the programs can be stored in a computer readable storage medium, and the process of the embodiment of each of the above-mentioned methods may be included when the programs are executed. The storage medium can be a diskette, an optical disk, a read-only memory (Read-Only Memory, ROM) or a random access memory (Random Access Memory, RAM) and the like.

The above descriptions should not be constructed as limitations to the scope of protection of the present invention, but are merely specific implementations. Any variations or replacements that can be readily apparent to the person skilled in the art within the technical scope disclosed by the present invention should fall within the scope of protection of the present invention. Therefore, the scope of protection of the present invention should be based on the scope of protection defined in the claims.

What is claimed is:

1. A rapid calculation method for a plaque stability index based on a medical image sequence, and the method comprises:

step 1, determining starting and ending positions of a vessel of interest, and defining a vessel between the starting and ending positions as a first-level segment;

step 2, acquiring a medical image sequence, and determining a plurality of feature moments of the vessel of interest in a deformation cycle, wherein the medical image sequence comprises complete images of a plurality of cycles of vessels;

step 3, performing lumen contour segmentation on the same vessel with different morphologies in frame images corresponding to different feature moments in step 2, determining starting and ending positions of a stenotic segment in the vessel of interest, and defining the stenotic segment as a second-level segment;

step 4, respectively establishing geometric models of a closed two-dimensional vascular lumen by using the first-level segment and the second-level segment in combination with a boundary contour line, and determining two regions of interest of the first-level segment and the second-level segment;

step 5, normalizing vessels with different lengths in different frame images by taking the length of a center line as a standard; and performing grid isomorphic discretization based on the normalized vessel length to establish a finite element model of a two-dimensional vascular lumen, firstly, performing coarse registration on the first-level segment, further performing fine registration on the second-level segment, and then, acquiring a displacement field function generated by a registration result;

step 6, applying the displacement field function to the finite element model of the two-dimensional vascular lumen acquired in step 5 and solving the displacement field function so as to acquire a cyclic time-dependent geometric deformation parameter of the lumen, a strain parameter of a lumen contour, and a cloud picture; and step 7, performing correlation analysis based on the cyclic time-dependent geometric deformation parameter of the lumen and the strain parameter of the lumen contour in step 6 in combination with plaque stability sample data, and performing calculation to obtain a plaque stability result.

2. The method according to claim 1, wherein the feature moments in step 2 are determined according to demarcation points of various wavebands of an electrocardiogram; or
a plurality of key time points are selected according to deformation features in the image sequence, and a cycle length and a time interval between every two adjacent time points are acquired, so that the feature moments are determined.

3. The method according to claim 1, wherein step 3 further comprises:
step 301, generating a center line of a vessel and a reference lumen as well as a series of diameter sequences in a longitudinal direction of the vessel and vertical to the center line while performing lumen contour segmentation on the vessel; and
step 302, setting a diameter stenosis percentage threshold, calculating a diameter stenosis percentage DS % (x) of the vessel of interest along a current position of the center line of the vessel, and taking starting and ending positions of a vascular segment meeting a requirement for the diameter stenosis percentage threshold as starting and ending positions of the second-level segment; wherein
a calculation formula of DS % (x) is as follows:

$$DS\ \%(x) = \left(1 - \frac{D_{act}(x)}{D_{ref}(x)}\right) \times 100 = \left(1 - \frac{D_{act}(x)}{(D_{pro} - D_{dis})x/L_{cen}}\right) \times 100;$$

in the formula, $D_{act}$ is an actual lumen diameter, $D_{ref}$ is a reference lumen diameter, $D_{pro}$ and $D_{dis}$ are respectively a near-end lumen diameter and a far-end lumen diameter, $L_{cen}$ is a total length of a center line, and x is a length of a center line from a current section position to a near end section.

4. The method according to claim 1, wherein step 4 further comprises:
establishing a feature space for image registration, wherein features comprised by the feature space comprises a lumen contour, a center line of a lumen and a diameter sequence; and
generating an equivalent diameter sequence after normalization.

5. The method according to claim 4, wherein step 5 further comprises:
performing feature search in the above feature space according to a preset search strategy; and
setting a similarity threshold of the first-level segment and the second-level segment of the vessel as a quantization standard in a registration process according to a preset similarity measurement criterion.

6. The method according to claim 1, wherein step 6 further comprises:
step 601, taking a geometric model of a two-dimensional lumen at a certain time point as an initial configuration, and performing structured grid discretization on the geometric model of the two-dimensional lumen at the certain time point; and
step 602, taking a finite element method as an image registration method, and when a similarity threshold of a stenotic segment and/or a normal segment is met, acquiring the displacement field function between adjacent moments until traversing a complete vascular deformation cycle so as to form a displacement path of a point cloud in a vascular deformation cycle.

7. The method according to claim 1, wherein in step 7, the strain parameter of the lumen contour comprises a maximum principal strain, a minimum principal strain, and an out-of-plane strain.

8. The method according to claim 1, wherein in step 7, the plaque stability is calculated by adopting the following formula:

$$S = \ln\left(c_1 * \frac{A}{A_0}\right) + \ln(c_2 * \overline{D_\varepsilon}) + \ln\left(c_3 * \frac{\overline{\varepsilon}}{\varepsilon_{max}}\right)$$

in the formula, A is a minimum stenosis area, $\overline{D_\varepsilon}$ is a mean value of a diameter strain on a minimum stenosis position, $\varepsilon_{max}$ and $\overline{\varepsilon}$ are respectively a maximum value and a mean value of a lumen contour strain, $C_i$, i=1, 2 and 3 are fitting parameters, and $A_0$ is the area of the reference lumen on the minimum stenosis position.

9. The method according to claim 5, wherein the normalization used is a bilinear interpolation method and a cubic convolution interpolation method; or the preset search strategy is a golden section method and a gradient descent method.

* * * * *